(12) United States Patent
Walker et al.

(10) Patent No.: US 10,675,101 B2
(45) Date of Patent: Jun. 9, 2020

(54) USER INTERFACE FOR ACTIVE DRIVE APPARATUS WITH FINITE RANGE OF MOTION

(71) Applicant: Auris Health, Inc., Redwood City, CA (US)

(72) Inventors: Sean Paul Walker, Fremont, CA (US); June Park, Palo Alto, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/268,798

(22) Filed: Feb. 6, 2019

(65) Prior Publication Data

US 2019/0167361 A1  Jun. 6, 2019

Related U.S. Application Data

(63) Continuation of application No. 15/054,870, filed on Feb. 26, 2016, now Pat. No. 10,206,746, which is a continuation of application No. 13/832,895, filed on Mar. 15, 2013, now Pat. No. 9,283,046.

(51) Int. Cl.
| | |
|---|---|
| *G05B 15/00* | (2006.01) |
| *A61B 34/00* | (2016.01) |
| *A61B 34/30* | (2016.01) |
| *G05B 15/02* | (2006.01) |

(52) U.S. Cl.
CPC .............. *A61B 34/25* (2016.02); *A61B 34/30* (2016.02); *A61B 34/74* (2016.02); *G05B 15/02* (2013.01); *A61B 2034/301* (2016.02); *A61B 2034/302* (2016.02); *G05B 2219/39439* (2013.01); *G05B 2219/39541* (2013.01)

(58) Field of Classification Search
CPC ......... A61B 34/25; A61B 34/74; A61B 34/30; A61B 2034/301; A61B 2034/302; G05B 15/02; G05B 2219/39541; G05B 2219/39439
USPC ....................................................... 700/275
See application file for complete search history.

(56) References Cited

U.S. PATENT DOCUMENTS

| | | |
|---|---|---|
| 4,771,262 A | 9/1988 | Reuss |
| 4,896,554 A | 1/1990 | Culver |
| 5,008,528 A | 4/1991 | Duchon |
| 5,176,310 A | 1/1993 | Akiyama et al. |
| 5,280,781 A | 1/1994 | Oku |
| 5,398,691 A | 3/1995 | Martin et al. |
| 5,408,409 A | 4/1995 | Glassman et al. |
| 5,499,632 A | 3/1996 | Hill et al. |
| 5,524,180 A | 6/1996 | Wang et al. |

(Continued)

FOREIGN PATENT DOCUMENTS

| | | |
|---|---|---|
| EP | 1 800 593 | 6/2007 |
| EP | 2 158 834 | 3/2010 |

(Continued)

*Primary Examiner* — Vu A Vu
(74) *Attorney, Agent, or Firm* — Knobbe, Martens, Olson & Bear LLP

(57) ABSTRACT

A system may include a controller configured to determine a user interface status, wherein the user interface status includes user interaction of a user interface. The controller may also be configured to determine a drive mechanism location relative to a first limit and a second limit and select a clutching location based on the user interface status and drive mechanism location.

19 Claims, 12 Drawing Sheets

(56) References Cited

U.S. PATENT DOCUMENTS

| | | |
|---|---|---|
| 5,526,812 A | 6/1996 | Dumoulin et al. |
| 5,631,973 A | 5/1997 | Green |
| 5,713,946 A | 2/1998 | Ben-Haim |
| 5,749,362 A | 5/1998 | Funda et al. |
| 5,762,458 A | 6/1998 | Wang et al. |
| 5,831,614 A | 11/1998 | Tognazzini et al. |
| 5,859,934 A | 1/1999 | Green |
| 5,876,325 A | 3/1999 | Mizuno et al. |
| 5,899,851 A | 5/1999 | Koninckx |
| 5,951,475 A | 9/1999 | Gueziec et al. |
| 5,963,770 A * | 10/1999 | Eakin .................. G03G 15/231 399/16 |
| 6,007,550 A | 12/1999 | Wang et al. |
| 6,016,439 A | 1/2000 | Acker |
| 6,038,467 A | 3/2000 | De Bliek et al. |
| 6,096,004 A | 8/2000 | Meglan et al. |
| 6,226,543 B1 | 5/2001 | Gilboa et al. |
| 6,259,806 B1 | 7/2001 | Green |
| 6,272,371 B1 | 8/2001 | Shlomo |
| 6,424,885 B1 | 7/2002 | Niemeyer et al. |
| 6,425,865 B1 | 7/2002 | Salcudean et al. |
| 6,466,198 B1 | 10/2002 | Feinstein |
| 6,468,265 B1 | 10/2002 | Evans et al. |
| 6,516,421 B1 | 2/2003 | Peters |
| 6,690,964 B2 | 2/2004 | Beiger et al. |
| 6,726,675 B1 | 4/2004 | Beyer |
| 6,856,827 B2 | 2/2005 | Seeley et al. |
| 7,155,315 B2 | 12/2006 | Niemeyer et al. |
| 7,594,925 B2 | 9/2009 | Danek |
| 8,180,114 B2 | 5/2012 | Nishihara et al. |
| 8,718,837 B2 | 5/2014 | Wang et al. |
| 8,971,597 B2 | 3/2015 | Zhao et al. |
| 9,014,851 B2 | 4/2015 | Wong et al. |
| 9,057,600 B2 | 6/2015 | Walker et al. |
| 9,241,767 B2 | 1/2016 | Prisco et al. |
| 9,271,663 B2 | 3/2016 | Walker et al. |
| 9,283,046 B2 * | 3/2016 | Walker .................. A61B 34/30 |
| 9,289,578 B2 | 3/2016 | Walker et al. |
| 9,498,291 B2 | 11/2016 | Balaji et al. |
| 9,503,681 B1 | 11/2016 | Popescu et al. |
| 9,504,604 B2 | 11/2016 | Alvarez |
| 9,532,840 B2 | 1/2017 | Wong et al. |
| 9,561,019 B2 | 2/2017 | Mihailescu et al. |
| 9,561,083 B2 | 2/2017 | Yu et al. |
| 9,566,414 B2 | 2/2017 | Wong et al. |
| 9,622,827 B2 | 4/2017 | Yu et al. |
| 9,629,595 B2 | 4/2017 | Walker et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,770,216 B2 | 9/2017 | Brown et al. |
| 9,788,910 B2 | 10/2017 | Schuh |
| 9,827,061 B2 | 11/2017 | Balaji et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,123,843 B2 | 11/2018 | Wong et al. |
| 10,130,345 B2 | 11/2018 | Wong et al. |
| 10,130,427 B2 | 11/2018 | Tanner et al. |
| 10,136,959 B2 | 11/2018 | Mintz et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,206,746 B2 | 2/2019 | Walker et al. |
| 10,219,874 B2 | 3/2019 | Yu et al. |
| 10,231,793 B2 | 3/2019 | Romo |
| 10,231,867 B2 | 3/2019 | Alvarez et al. |
| 10,346,976 B2 | 7/2019 | Averbuch |
| 10,434,660 B2 | 10/2019 | Meyer |
| 10,464,209 B2 | 11/2019 | Ho et al. |
| 10,470,830 B2 | 11/2019 | Hill |
| 10,482,599 B2 | 11/2019 | Mintz et al. |
| 2002/0077533 A1 | 6/2002 | Bieger et al. |
| 2002/0120188 A1 | 8/2002 | Brock et al. |
| 2002/0161280 A1 | 10/2002 | Chatenever et al. |
| 2004/0047044 A1 | 3/2004 | Dalton |
| 2004/0263535 A1 | 12/2004 | Birkenbach et al. |
| 2005/0085714 A1 | 4/2005 | Foley et al. |
| 2005/0193451 A1 | 9/2005 | Quistgaard et al. |
| 2006/0025676 A1 | 2/2006 | Viswanathan et al. |
| 2006/0079745 A1 | 4/2006 | Viswanathan et al. |
| 2006/0095022 A1 | 5/2006 | Moll et al. |
| 2006/0146010 A1 | 7/2006 | Schneider |
| 2006/0173290 A1 | 8/2006 | Lavallee et al. |
| 2007/0083098 A1 | 4/2007 | Stern et al. |
| 2007/0138992 A1 | 6/2007 | Prisco et al. |
| 2007/0144298 A1 | 6/2007 | Miller |
| 2007/0185486 A1 | 8/2007 | Hauck et al. |
| 2008/0027313 A1 | 1/2008 | Shachar |
| 2008/0097465 A1 | 4/2008 | Rollins et al. |
| 2008/0108870 A1 | 5/2008 | Wiita et al. |
| 2008/0140087 A1 | 6/2008 | Barbagli et al. |
| 2008/0159653 A1 | 7/2008 | Dunki-Jacobs et al. |
| 2008/0183068 A1 | 7/2008 | Carls et al. |
| 2008/0183188 A1 | 7/2008 | Carls et al. |
| 2008/0306490 A1 | 12/2008 | Lakin et al. |
| 2009/0248036 A1 | 10/2009 | Hoffman et al. |
| 2009/0259230 A1 | 10/2009 | Khadem |
| 2009/0259412 A1 | 10/2009 | Brogardh |
| 2009/0326322 A1 | 12/2009 | Diolaiti |
| 2009/0326556 A1 | 12/2009 | Diolaiti et al. |
| 2010/0019890 A1 | 1/2010 | Helmer et al. |
| 2010/0039506 A1 | 2/2010 | Sarvestani et al. |
| 2010/0076263 A1 | 3/2010 | Tanaka |
| 2010/0121269 A1 | 5/2010 | Goldenberg |
| 2010/0125284 A1 | 5/2010 | Tanner et al. |
| 2010/0161129 A1 | 6/2010 | Costa et al. |
| 2010/0204613 A1 | 8/2010 | Rollins et al. |
| 2010/0225209 A1 | 9/2010 | Goldberg |
| 2010/0286847 A1 | 11/2010 | Cerchie et al. |
| 2010/0328455 A1 | 12/2010 | Nam et al. |
| 2011/0021926 A1 | 1/2011 | Spencer |
| 2011/0113852 A1 | 5/2011 | Prisco |
| 2011/0118748 A1 | 5/2011 | Itkowitz |
| 2011/0118752 A1 | 5/2011 | Itkowitz et al. |
| 2011/0118753 A1 | 5/2011 | Itkowitz et al. |
| 2011/0130718 A1 | 6/2011 | Kidd et al. |
| 2011/0196199 A1 | 8/2011 | Donhowe et al. |
| 2011/0235855 A1 | 9/2011 | Smith |
| 2011/0238010 A1 | 9/2011 | Kirschenman et al. |
| 2011/0248987 A1 | 10/2011 | Mitchell |
| 2011/0276058 A1 | 11/2011 | Choi et al. |
| 2011/0306873 A1 | 12/2011 | Shenai et al. |
| 2012/0059392 A1 | 3/2012 | Diolaiti |
| 2012/0071752 A1 | 3/2012 | Sewell |
| 2012/0071891 A1 | 3/2012 | Itkowitz et al. |
| 2012/0071892 A1 | 3/2012 | Itkowitz et al. |
| 2012/0071894 A1 | 3/2012 | Tanner et al. |
| 2012/0075638 A1 | 3/2012 | Rollins et al. |
| 2012/0078053 A1 | 3/2012 | Phee et al. |
| 2012/0103123 A1 | 5/2012 | McInroy et al. |
| 2012/0158011 A1 | 6/2012 | Sandhu |
| 2012/0191107 A1 | 7/2012 | Tanner et al. |
| 2012/0203067 A1 | 8/2012 | Higgins et al. |

(56) References Cited

U.S. PATENT DOCUMENTS

| | | |
|---|---|---|
| 2012/0253276 A1 | 10/2012 | Govari et al. |
| 2012/0296161 A1 | 11/2012 | Wallace et al. |
| 2012/0314022 A1 | 12/2012 | Jo |
| 2013/0018306 A1 | 1/2013 | Ludwin |
| 2013/0060146 A1 | 3/2013 | Yang et al. |
| 2013/0165854 A1 | 6/2013 | Sandhu et al. |
| 2013/0317519 A1 | 11/2013 | Romo et al. |
| 2014/0111457 A1 | 4/2014 | Briden et al. |
| 2014/0142591 A1 | 5/2014 | Alvarez et al. |
| 2014/0222204 A1 | 8/2014 | Kawashima |
| 2014/0257334 A1 | 9/2014 | Wong et al. |
| 2014/0264081 A1 | 9/2014 | Walker et al. |
| 2014/0275988 A1 | 9/2014 | Walker et al. |
| 2014/0276392 A1 | 9/2014 | Wong et al. |
| 2014/0276394 A1 | 9/2014 | Wong et al. |
| 2014/0276646 A1 | 9/2014 | Wong et al. |
| 2014/0276934 A1 | 9/2014 | Balaji et al. |
| 2014/0276937 A1 | 9/2014 | Wong et al. |
| 2014/0276938 A1 | 9/2014 | Hsu et al. |
| 2014/0277333 A1* | 9/2014 | Lewis ............... A61M 25/0113 623/1.11 |
| 2014/0277747 A1 | 9/2014 | Walker et al. |
| 2014/0357984 A1 | 12/2014 | Wallace et al. |
| 2014/0364870 A1 | 12/2014 | Alvarez et al. |
| 2015/0018622 A1 | 1/2015 | Tesar et al. |
| 2015/0051592 A1 | 2/2015 | Kintz |
| 2015/0105747 A1 | 4/2015 | Rollins et al. |
| 2015/0142013 A1 | 5/2015 | Tanner et al. |
| 2015/0157191 A1 | 6/2015 | Phee et al. |
| 2015/0164594 A1 | 6/2015 | Romo et al. |
| 2015/0164596 A1 | 6/2015 | Romo |
| 2015/0223902 A1 | 8/2015 | Walker et al. |
| 2015/0224845 A1 | 8/2015 | Anderson et al. |
| 2015/0265807 A1 | 9/2015 | Park et al. |
| 2015/0290454 A1 | 10/2015 | Tyler et al. |
| 2015/0314110 A1 | 11/2015 | Park |
| 2015/0335480 A1 | 11/2015 | Alvarez et al. |
| 2015/0375399 A1 | 12/2015 | Chiu et al. |
| 2016/0001038 A1 | 1/2016 | Romo et al. |
| 2016/0026253 A1 | 1/2016 | Bradski et al. |
| 2016/0059412 A1 | 3/2016 | Oleynik |
| 2016/0098095 A1 | 4/2016 | Gonzalez-Banos et al. |
| 2016/0183841 A1 | 6/2016 | Duindam et al. |
| 2016/0202053 A1 | 7/2016 | Walker et al. |
| 2016/0213436 A1 | 7/2016 | Inoue |
| 2016/0213884 A1 | 7/2016 | Park |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0314710 A1 | 10/2016 | Jarc |
| 2016/0314716 A1 | 10/2016 | Grubbs |
| 2016/0314717 A1 | 10/2016 | Grubbs |
| 2016/0324580 A1 | 11/2016 | Esterberg et al. |
| 2016/0374541 A1 | 12/2016 | Agrawal et al. |
| 2017/0007337 A1 | 1/2017 | Dan |
| 2017/0065356 A1 | 3/2017 | Balaji et al. |
| 2017/0100084 A1 | 4/2017 | Walker et al. |
| 2017/0100199 A1 | 4/2017 | Yu et al. |
| 2017/0113019 A1 | 4/2017 | Wong et al. |
| 2017/0119481 A1 | 5/2017 | Romo et al. |
| 2017/0143429 A1 | 5/2017 | Richmond et al. |
| 2017/0165011 A1 | 6/2017 | Bovay et al. |
| 2017/0172664 A1 | 6/2017 | Weingarten et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0056044 A1 | 3/2018 | Choi et al. |
| 2018/0078321 A1 | 3/2018 | Liao |
| 2018/0177383 A1 | 6/2018 | Noonan et al. |
| 2018/0177556 A1 | 6/2018 | Noonan |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0090969 A1 | 3/2019 | Jarc et al. |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0151032 A1 | 5/2019 | Mustufa et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |

FOREIGN PATENT DOCUMENTS

| | | |
|---|---|---|
| WO | WO 03/086190 | 10/2003 |
| WO | WO 08/049088 | 4/2008 |
| WO | WO 10/025522 | 3/2010 |

* cited by examiner

USER INTERFACE FOR ACTIVE DRIVE APPARATUS WITH FINITE RANGE OF MOTION

This application is a Continuation of U.S. patent application Ser. No. 15/054,870, filed Feb. 26, 2016, entitled "USER INTERFACE FOR ACTIVE DRIVE APPARATUS WITH FINITE RANGE OF MOTION," which is a Continuation of U.S. patent application Ser. No. 13/832,895, filed Mar. 15, 2013, now U.S. Pat. No. 9,283,046, entitled "USER INTERFACE FOR ACTIVE DRIVE APPARATUS WITH FINITE RANGE OF MOTION," the entireties of which are herein incorporated by reference.

BACKGROUND

Robotic surgical systems and devices are well suited for use in performing minimally invasive medical procedures as opposed to conventional techniques that require large incisions to permit the surgeon's hands access into the patient's body cavity. Advances in technology have led to significant changes in the field of medical surgery such that minimally invasive surgeries (MIS) have become increasingly popular.

As opposed to traditional open surgery, MIS may typically be performed by entering the body through the skin, blood vessels, gastrointestinal tract, or an anatomical opening utilizing small incisions made on the patient's body. However, such procedures (e.g., endovascular, laparoscopic, arthroscopic, coronary, etc.) require manipulation and control over a variety of devices, ranging from guidewires and microcatheters to balloons and stents.

In order to manipulate the medical instruments (e.g., a guidewire), medical professionals have traditionally used devices which allow the professional to apply a torque to a guidewire while inside the patient's body. Torqueing the guidewire allows the medical professional to change the spatial orientation of the tip of the guidewire while maneuvering the patient's anatomy, e.g., to insert or retract the guidewire, or to rotate the guidewire.

Due to the complexities of MIS procedures, for example robotically controlled endovascular procedures, manipulation and control is required over a variety of medical devices (e.g., guidewires, stents, etc.). As a result, it is often challenging to advance or retract a full variety of medical instruments required by robotic surgical systems during medical procedures. Moreover, it is difficult to continuously drive a guidewire in a discontinuous system. Specifically, once the driver carrying the guidewire reaches its physical limits or the end of its range of motion, the guidewire may need to be released and then re-gripped or clutched in order to further drive the guidewire into a patient. During such clutching, the movement of the guidewire may be temporarily restricted.

As such, there is a need for a system that may conveniently perform clutching with minimal interruptions during the medical procedure.

SUMMARY

A system may include a controller configured to determine a user interface status, wherein the user interface status includes user interaction of a user interface. The controller may also be configured to determine a drive mechanism location relative to a first limit and a second limit and select a clutching location based on the user interface status and drive mechanism location.

A method may include determining a user interface status, the user interface status including a user interaction of a user interface, determining a drive mechanism location relative to a first limit and a second limit along a slave device; and determining whether to clutch the slave device based on the user interface status and drive mechanism location.

A non-transitory computer readable medium tangibly embodying computer-executable instructions, include instructions for determining a user interface status, the user interface status including a user interaction of a user interface, determining a drive mechanism location relative to a first limit and a second limit along a slave device, and determining whether to clutch the slave device based on the user interface status and drive mechanism location.

BRIEF DESCRIPTION

DETAILED DESCRIPTION

Figure 1:
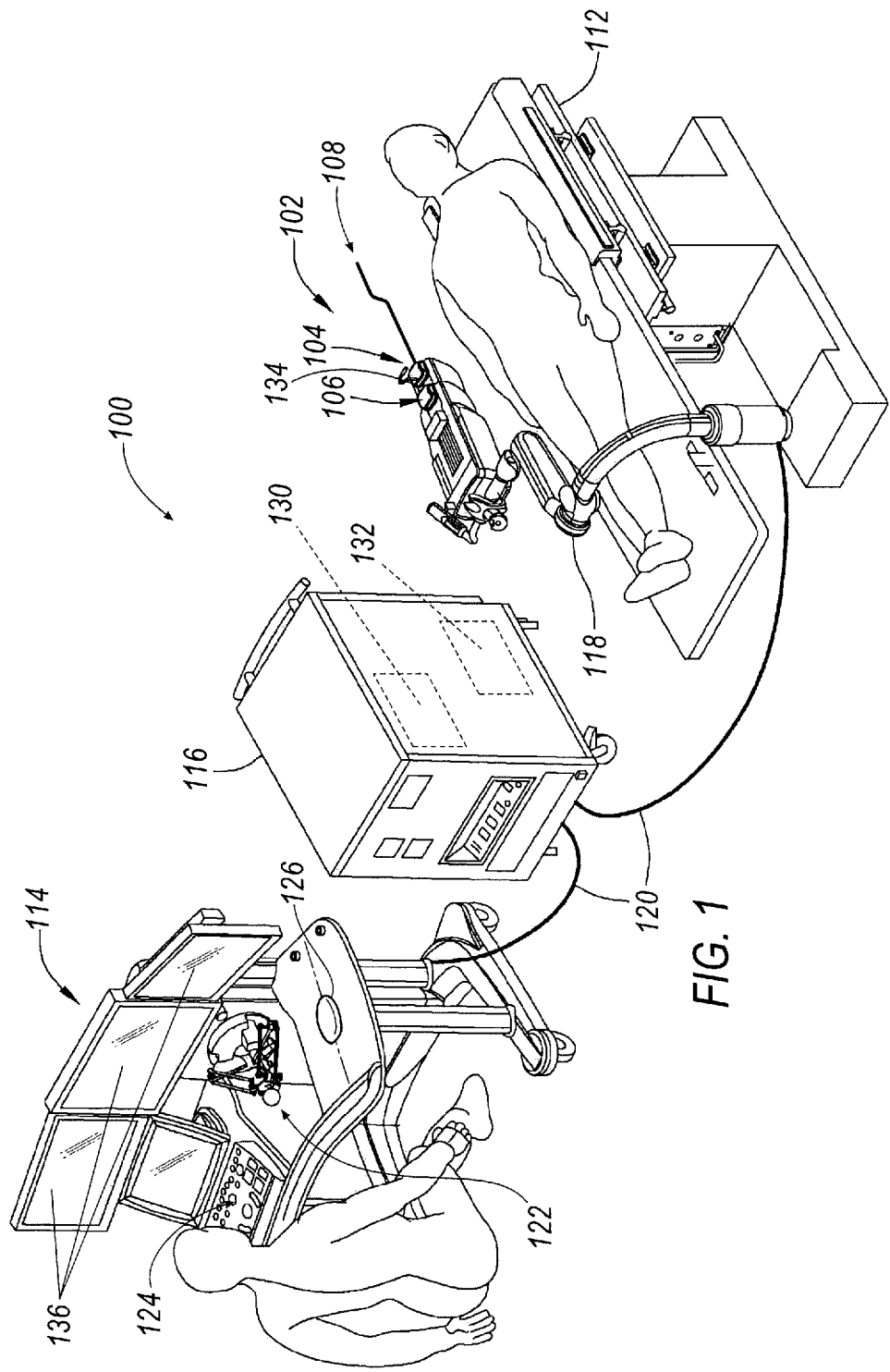
FIG. 1 illustrates an exemplary robotically controlled surgical system.

FIG. 1 illustrates an exemplary robotically controlled surgical system 100 in which an apparatus, a system, and/or method may be implemented according to various exemplary illustrations. System 100 may include a robotic catheter assembly 102 having a robotic or outer steerable complement, otherwise referred to as a sheath instrument (generally referred to as "sheath" or "sheath instrument") and/or an inner steerable component, otherwise referred to as a robotic catheter or guide or catheter instrument 106 (generally referred to as "catheter 106" or "catheter instrument 106"). The catheter instrument 106 may further include a guide wire 108 extendable beyond a distal end of the catheter instrument 106. Catheter assembly 102 is controllable using a robotic instrument driver (generally referred to as "instrument driver"). During use, a patient is positioned on an operating table or surgical bed 112 (generally referred to as "operating table") to which robotic instrument driver is coupled or mounted. In the illustrated example, system 100 includes an operator workstation 114, an electronics rack 116 and associated bedside electronics box (not shown), a setup joint mounting brace 118, and instrument driver. A surgeon is seated at operator workstation 114 and can monitor the surgical procedure, patient vitals, and control one or more catheter devices.

System components may be coupled together via a plurality of cables or other suitable connectors 120 to provide for data communication, or one or more components may be equipped with wireless communication components to reduce or eliminate cables 120. Communication between components may also be implemented over a wireless network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

The operator workstation 114 may include a computer monitor configured to display a three dimensional object, such as a representation of the catheter instrument 106 and guide wire 108. The catheter instrument 106 and guide wire 108 may be displayed within or relative to a three dimensional space, such as a body cavity or organ, e.g., a chamber of a patient's heart.

The operator workstation 114 may further provide for control of the catheter 106 and guide wire 108. As one example, the operator workstation 114 may include at least one user interface. The user interface may include controls such as a joystick 122, a keyboard 124, input device 115 and/or a mouse 126. While specific examples are described below with one of these interfaces, each interface, although not explicitly described, may be applied to the various examples. The workstation 114 may also include at least one display 136. The display may be configured to display various aspects of the medical procedure to the surgeon. The display may be any type of monitor, computer screen, television, etc.

The catheter 106 may be controlled using the user interface allowing for steering of the distal tip of the guide catheter 106 as viewed on the computer monitor display, while the guide wire 108 may be controlled using the keyboard type input device 124. The user interface may further include various sensors to detect the position of user interface and to provide signals to the controller 130 that are interpreted as commands.

A variation of the user interfaces (e.g., joystick 122, mouse 126, keyboard 124, input device 115 (shown in FIG. 2C.)) of FIG. 1 may include controls for the sheath catheter and elongate member manipulator. The keyboard type input device 124 may include bend, insert and rotate controls to steer the sheath catheter, as well as rotate and insert controls to control the elongate member manipulator. In alternative variations, the distal tip of the guide wire 108 may be controlled using the joystick 122 while the guide and sheath catheters may be controlled by the keyboard type input device 124.

Figure 3:
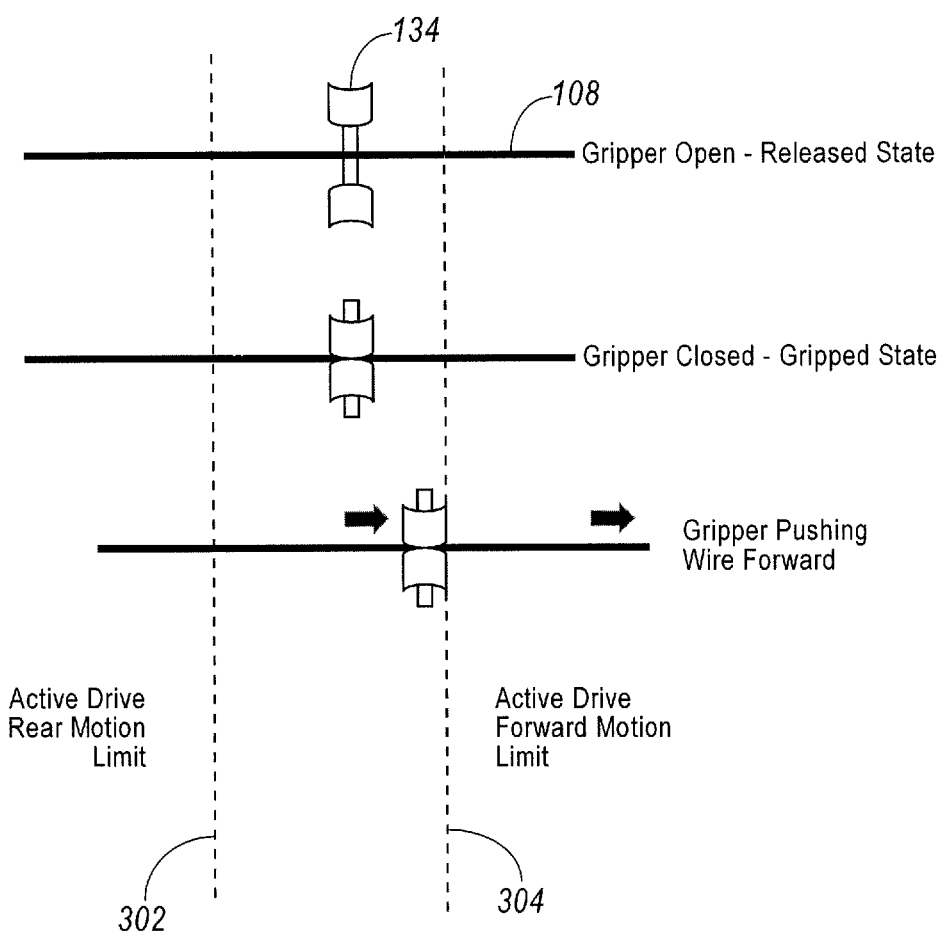
FIG. 3 illustrates an exemplary clutching system.

The catheter assembly 102 may have the ability to infinitely insert and/or roll a guidewire. The assembly 102 may include a drive mechanism 104 configured to move the wire. This drive mechanism 104 may include at least one gripper 134 within a housing configured to grip and move the wire. The housing may be configured to move along a predefined axis at the catheter assembly 102 to drive or retract the wire 108. The gripper 134 may be received by an instrument driver. The instrument driver, however, may only be capable of inserting/rolling for a finite range. Examples of this range are shown in FIG. 3 and described further below. Due to the limited range of motion, the gripper 134 may only be capable of driving the wire 108 forward to a certain point until it must release, retract and re-grip (i.e. clutch) the wire 108 before further driving it.

Thus, to facilitate movement beyond a range of motion, i.e., an "infinite" drive of a system having a finite range of motion, a clutching mechanism may be used. The clutching mechanism may include a stationary gripper configured to temporarily grab the wire 108 to hold it steady while a main gripper releases the wire 108, resets itself, and re-grips the wire 108. However, during this 'clutching', the user may experience a delay in response from the guide wire 108. That is, the wire 108 may not drive or rotate during this clutching. The clutching, may, therefore affect the operation of the catheter system 102.

A controller 130 may be configured to optimize the clutching mechanism within the system. For example, it may selectively clutch upon determining that further drive is not necessary. It may also determine an appropriate clutch location. That is, where along an axis a system should clutch. Moreover, the user interface may be configured to display to the user that clutching is occurring to further indicate to the user that movement of the wire 108 may be temporarily suspended.

The controller 130 may be in communication with a database 132. The database may be configured to store rules associated with the controller 130 and the user interfaces whereby the rules may be applied to certain signals received from the controller 130. These rules may be interpreted by the controller to determine when and how far the drive mechanism should clutch the wire 108. Examples of these rules may be discussed herein. The controller 130 may be located within the workstation 114 or at the electronics rack 116. The controller 130 may be a processor configured to receive data from the user interface and the catheter assembly 102. This data may be used to determine how, when and where the clutching mechanism should clutch. This process is described in more detail below.

Figure 2A:
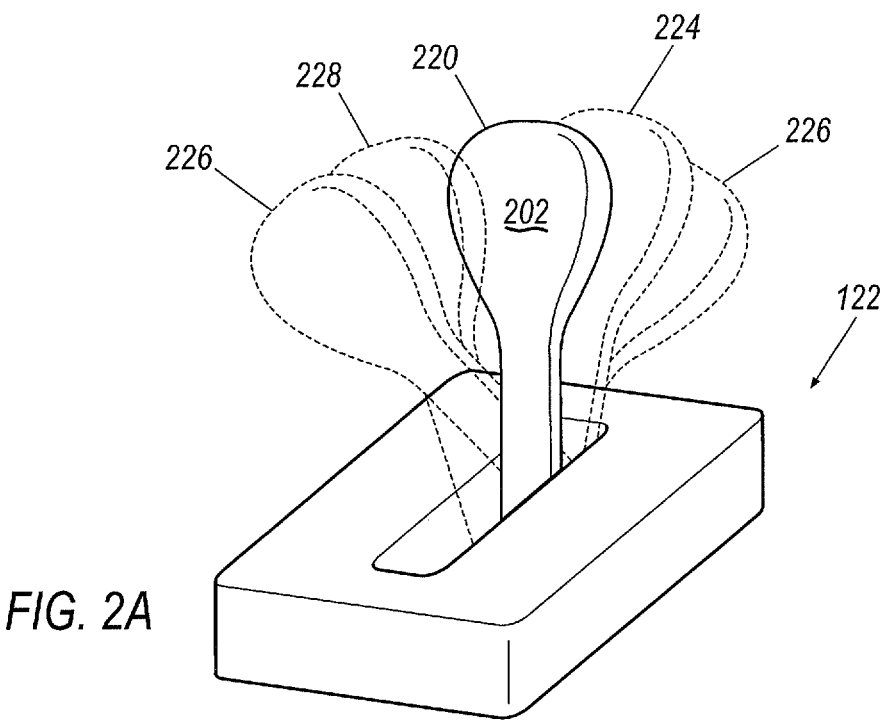
FIGS. 2A-2D illustrate exemplary user interfaces.

FIG. 2A shows an exemplary joystick 122. The joystick 122 may include a control member 202 configured to move about a pivot point. The control member 202 may move radially about the pivot point so as to move forward and backward along an axis at the pivot point. As shown in FIG. 2A, the control member 202 may move between a plurality of positions. For example, the control member 202 may be in a normal position 220. The control member 202 may be in any number of forward positions 222, 224 and backward positions 226, 228, as shown in phantom. The forward positions may 222, 224 include a full forward position 222 and a partial forward position 224. Similarly, the backward positions 226, 228 may include a full backward 226 position and a partial backward position 228. The control member 202 may engage any number of sensors within the joystick 122. The engaged sensors may indicate to the controller 130 the position of the control member 202. This position determines at least the drive of the wire 108. That is, if the control member 202 is in a normal position 220, the wire 108 may be stationary. If the control member 202 is in a partial forward position 224, the wire 108 may be instructed to move forward at a moderate speed. If the wire is at a full backward position 226, the wire 108 may be instructed to move backward at an increased speed. Additionally, velocity may be calculated by comparing a position of the control member 202 at a first time with a position of the control member 202 at a second time. Thus, the joystick 122 may be configured to control the velocity of the wire 108. The joystick 122 may also control the side-to-side and vertical motion of wire 108.

Figure 2B:
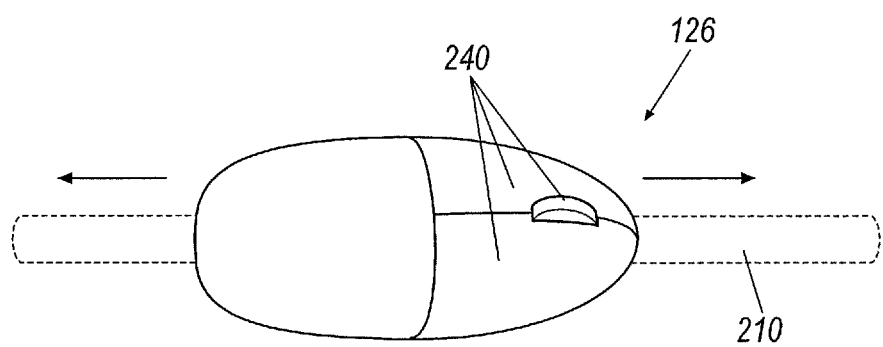

FIG. 2B shows an exemplary mouse 126. The mouse 126 may be a pointing device capable of driving and directing the wire 108. The mouse 126 may move along a flat surface, such as a desk of the workstation 114. It may include one or more buttons 240 and be configured to detect at least two dimensional motion relative to the flat surface. The mouse 126 may be used to control the drive of the wire 108 in a one-to-one manner. That is, lateral movement of the mouse 126 may correlate directly with lateral movement of the wire 108. The mouse 126 may move along a line 210. The line 210 may be an imaginary line depicting the lateral limits of the mouse 126. For example, the length at which a mouse 126 may be pushed in one direction may be limited by the amount of surface at a workstation 114. Further, the cord length of a mouse 126, or simply the doctor's arm reach, may limit the length that a mouse 126 may move. The mouse 126, as explained, may control the drive of the wire 108. It may also control the velocity of the wire 108. Additionally, and as discussed below, one of the buttons 240 included in the mouse 126 may also control the gripping/clutching of the drive mechanism 104.

Figure 2C:
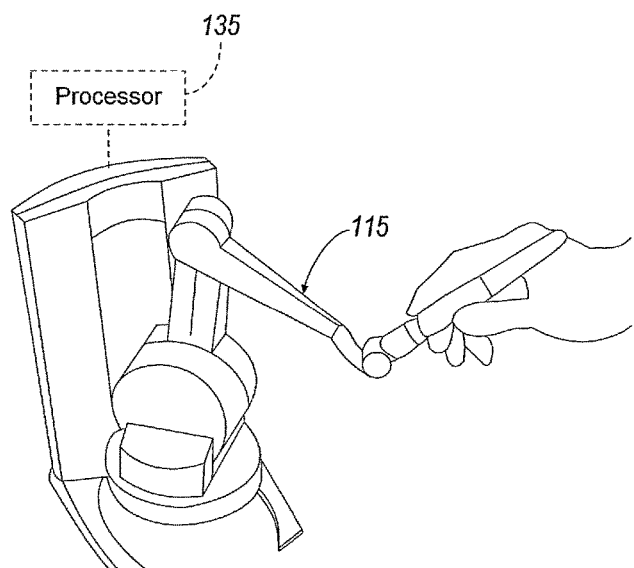

FIG. 2C shows another exemplary input device that may be configured to allow a surgeon to drive the wire 108. The input device 115 may be configured to receive an input from the surgeon based on the way the surgeon physically manipulates the position of the input device 115. As shown, the input device 115 provides the surgeon with multiple degrees of freedom, each associated with a different movement of the catheter assembly 102, so that the surgeon can control the catheter assembly 102 as if the surgeon were manipulating the position and orientation of the catheter assembly 102 directly.

The input device 115 may include a processor 135 configured to interpret the input from the surgeon and generate and output corresponding signals to the controller. For clarity, the processor 135 is shown outside the input device 115. In some possible approaches, however, the processor 135 may be embedded in the input device 115. The processor 135 may be configured to generate an advance signal when the surgeon indicates a desire to push the catheter assembly 102 into the patient's body. The processor 135 may be further configured to generate a retract signal when the surgeon indicates a desire to pull at least a portion of the catheter assembly 102 from the patient's body. Moreover, the processor 135 may be configured to generate a rotate signal when the surgeon indicates a desire to rotate the catheter assembly 102. As discussed above, the surgeon desire for controlling the catheter assembly 102 may be expressed through movement of the input device 115. The processor 135 may interpret these movements based on the outputs of various sensors of the input device 115 and may send the interpretation to the controller 130.

Thus, the user interface (joystick 122, the mouse 126 and/or input device 115) may be used to drive the wire 108 in FIG. 3. Each may control when the wire 108 is driven and retracted, as well as the rate at which it does so. In some active drive systems, it may not be possible to continually drive the wire 108. This may be due, at least in part, to limits of the catheter assembly 102 and/or the user interface. For example, the catheter assembly 102 may have a limited length by which a gripper 134 of the assembly 102 may be capable of driving the wire 108. These limits 302, 304 may be at least partially due to the length of the instrument 106. Once the driver of the instrument has reached the end of the assembly 102, it cannot further drive the wire 108. The same is true for when the driver of the assembly 102 has reached the opposite end and thus cannot retract the wire 108 any further. Thus, in some active drive systems, it may not be possible to continually move the wire 108 in one direction. The instrument 106 may need to release the wire 108, adjust one of the drivers and then re-grip the wire 108 to continue to move the wire 108. That is, the instrument 106 may need to re-grip the wire 108 at another position along the wire 108 in order to continue driving the wire (i.e. perform clutching).

While the catheter assembly 102 may limit the range of continuous wire drive, the user interface may also limit wire drive as well. For example, line 210 may indicate the limits of a mouse 126. The joystick 122 may also have limits in that it may only be pushed forward or backward to an extent. Similarly, the input device 115 may also have a limited range of motion.

The wire may be selectively gripped by a gripper 134. As shown in FIG. 1, two parallel grippers 134 may be used to frictionally engage the wire 108. While one driver is gripping the wire 108, another may be in an un-gripped, or released state. The grippers 134 may move along the catheter assembly 102 to drive the wire 108 into the patient. The grippers 134, although shown as including two parallel grippers, may also include other mechanisms such as sleeves configured to frictionally engage the wire 108 upon clamping. Additionally or alternatively, washers and other cylindrical holders may also be used.

Figure 2D:
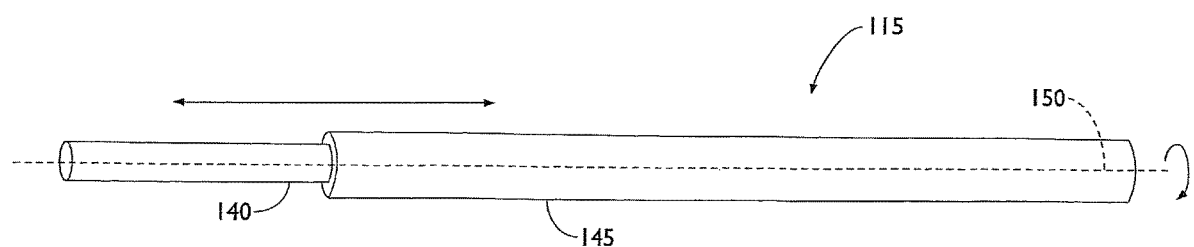

FIG. 2D illustrates exemplary components of the input device 115 for manipulating the position and orientation of the catheter assembly 102. As shown in FIG. 2, the input device 115 includes an inner member 140 and an outer member 145. The inner member 140, as illustrated, has a generally cylindrical shape that defines an axis 150. The outer member 145 is coaxially disposed on the inner member 140 and is configured to rotate about and move along the axis 150. This movement of the outer member 145 relative to the inner member 140 may be detected and signals representing the movement may be output to the processor 135 for the processor 135 to determine the surgeon's desired operation of the catheter assembly 102. Specifically, rotating the outer member 145 about the axis 150 may indicate the surgeon's desire to rotate the catheter 120, the guide wire 125, or both. Moving the outer member 145 along the axis 150 may indicate the surgeon's desire to advance (e.g., push) or retract (e.g., pull) the catheter 120, the guide wire 125, or both relative to the patient's body.

Described with respect to FIGS. 3-11 is a drive mechanism 104 for controlling a wire 108. The drive mechanism 104 is facilitated by coordinating the drive mechanism location, or grip location, of a wire 108 with the user interaction at the user interface. The controller 130 may facilitate when and where to perform re-gripping based on detected user interaction at the user interface.

FIG. 3 shows exemplary gripper states and motion limits for the drive mechanism 104. A wire 108 may be located between at least one gripper 134. This gripper 134, as explained, may be located within the driver housing of a catheter assembly 102. The housing may be configured to move along a predefined axis at the catheter assembly 102 to drive or retract the wire 108. The gripper 134 may be in a released state or a gripped state, as shown in FIG. 3. In a gripped state, the gripper 134 may be stationary, but gripping the wire 108 at the drive mechanism location. The gripper 134 may also be configured to grip and move the wire 108.

FIG. 3 also shows an active drive rear motion limit and an active drive forward motion limit. These are referred to hereinafter as a first limit 302 and a second limit 304. As explained, these limits may correspond to physical limits 302, 304 defining a range of motion of the catheter assembly 102.

Figure 4:
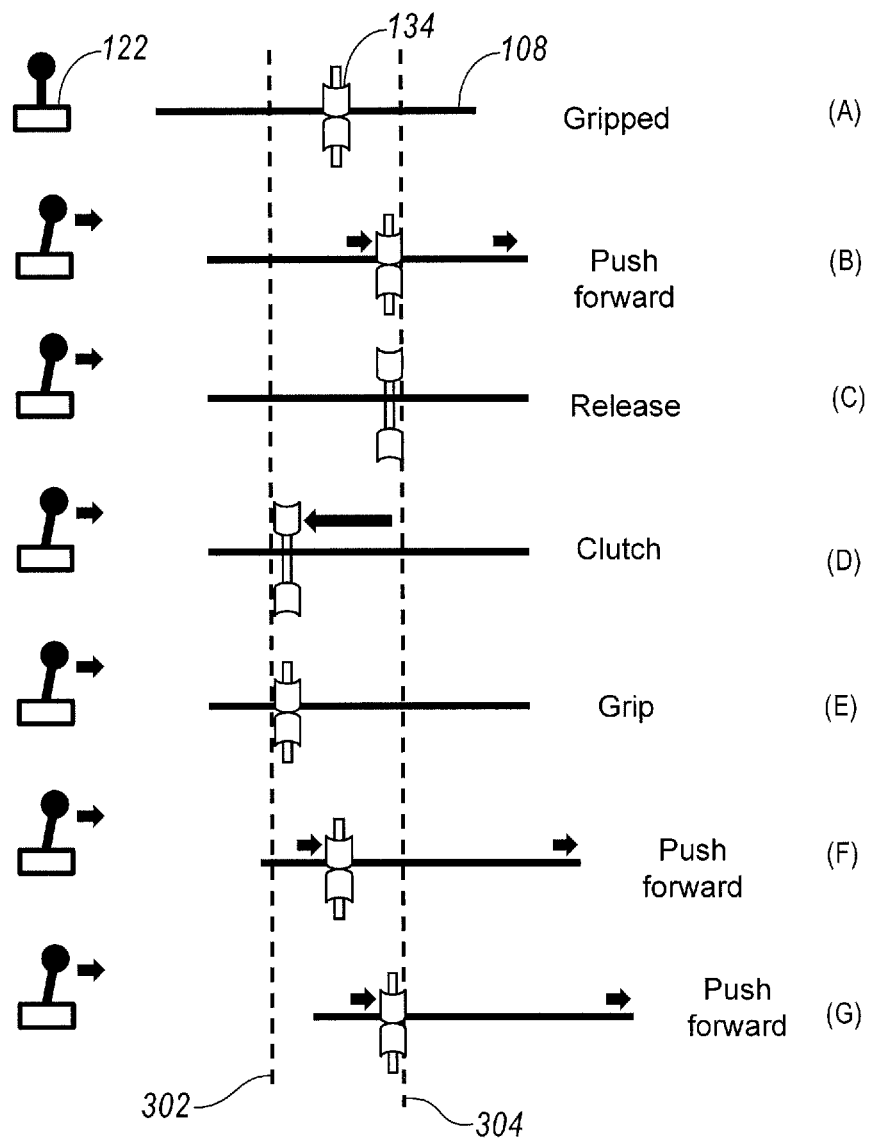
FIG. 4 illustrates an exemplary process for a constant velocity signal.

FIG. 4 shows an exemplary process when receiving a constant velocity signal. In this example, a constant drive signal may be sent from the user interface (e.g., joystick 122.) That is, the wire 108 may be instructed to drive (e.g., move forward) at a constant velocity/speed. Due to the second limit 304, the gripper 134 may only be capable of driving the wire 108 forward to a certain point until it must release, retract and re-grip (i.e. clutch) the wire 108 before further driving it.

Beginning at index (A), the gripper 134 is gripped at a central position between the first and second limits 302, 304. The joystick 122 is in the normal position 220, (e.g., stationary position.) At index (B), the joystick 122 may be pushed into one of the forward positions 222, 224. In response, the gripper 134 may push the wire 108 forward until the gripper 134 reaches the second limit 304. At this limit 304, the gripper 134 may no longer push forward. The gripper 134 then releases the wire 108 at index (C) and moves backwards to the first limit 302 at index (D). Thus, at index (D) the gripper 134 is configured to clutch the wire 108 in order to continue the wire drive. At index (E) the gripper 134 re-grips the wire 108 and begins to push the wire 108 forward at index (F). At index (G) the gripper 134 has once again reached its limit and must once again re-clutch in order to continue to drive the wire 108.

Figure 5:
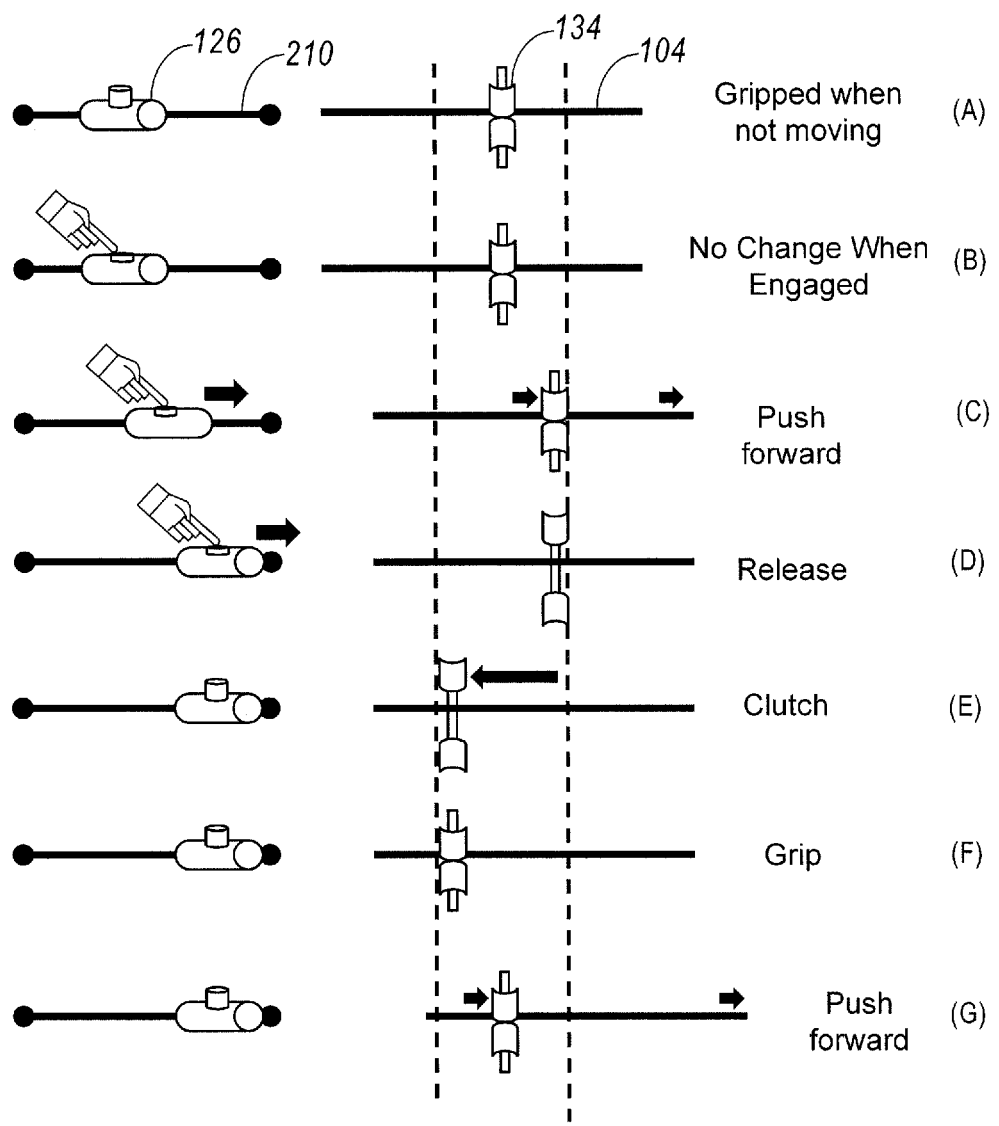
FIG. 5 illustrates an exemplary relative position control process.

FIG. 5 shows an exemplary relative position control process. While the figures may depict a mouse-like icon, the joystick 122 and input device 115 may also be applied in the various situations. In this example, a surgeon may use a user interface to continually drive a wire 108. The user interface, such as the mouse 126, may include a push-button 240. The push button 240 may be used by the surgeon to initiate the drive. However, the depression of the button 240 may not necessarily correlate with the gripping of the gripper 134. That is, the gripper 134 does not necessarily mimic the button 240.

At index (A) the button 240 of the mouse 126 may not be depressed but the gripper 134 may be in a gripped state in a central location. At index (B) the surgeon may depress the button 240 and begin to move the mouse 126 forward. At index (C) the surgeon may continue to push the mouse 126 forward. However, the gripper 134 may reach the second limit 304. At index (D) the gripper 134 may release and at index (E) the gripper 134 may clutch at the first limit 302. At index (F) the gripper 134 may grip the wire 108 and at index (G) the gripper 134 may resume pushing the wire 108 forward. This may lead to a frustrating driving experience because the mechanism is not truly following the user intent.

Figure 6:
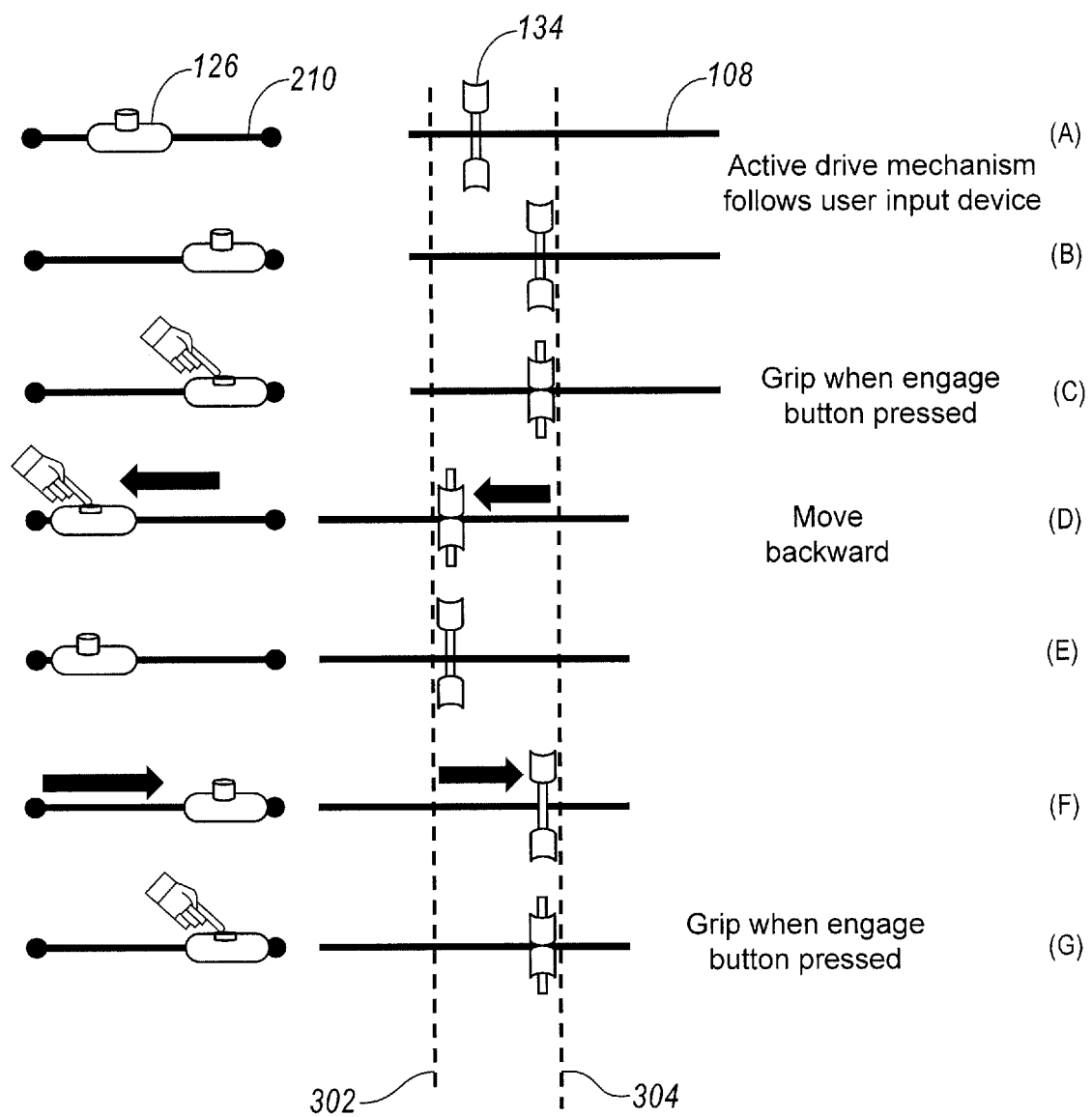
FIG. 6 illustrates an exemplary relative position control process where the drive mechanism mimics that of the user interface.
Figure 7:
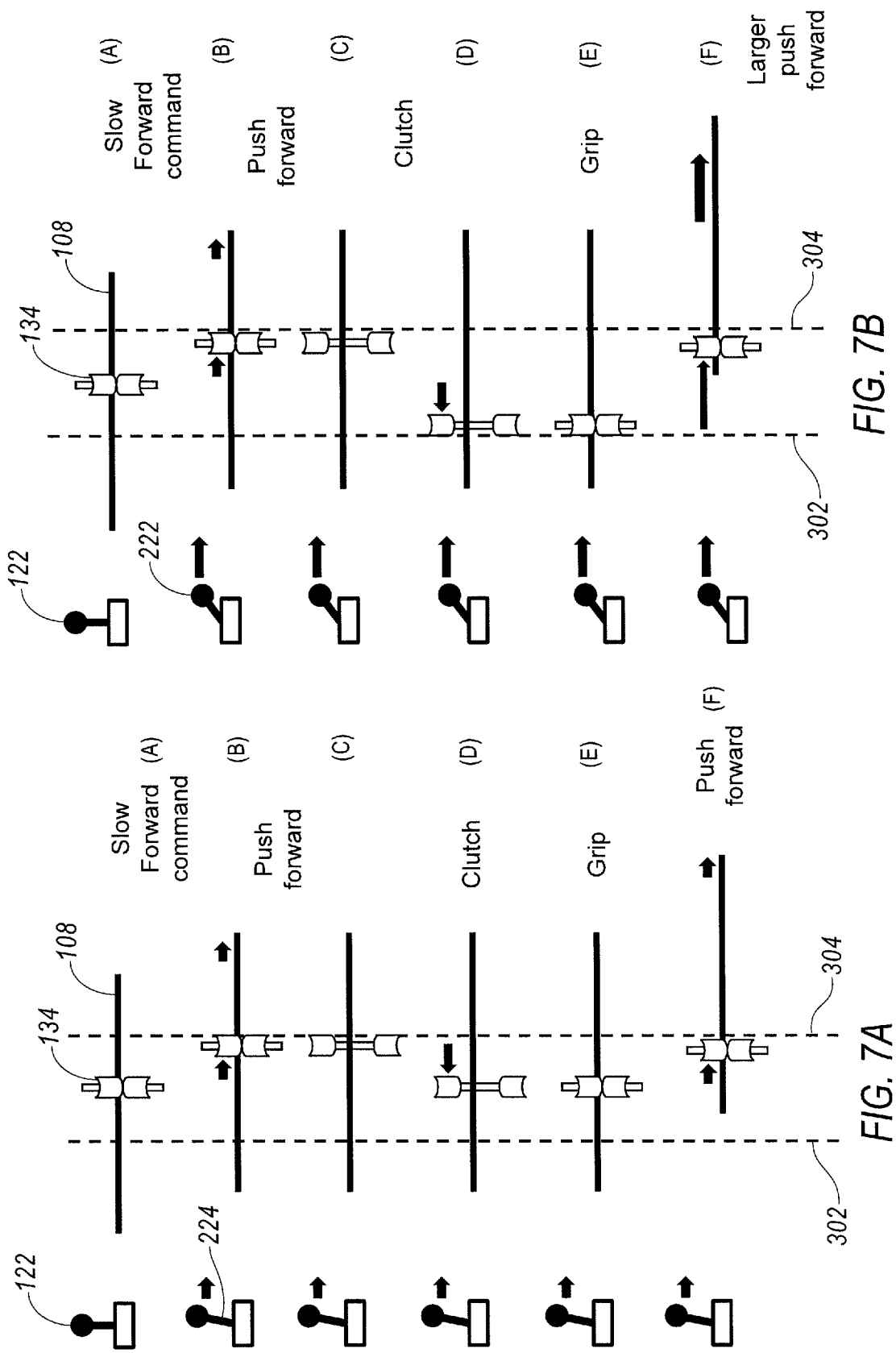
FIGS. 7A and 7B illustrate an exemplary dynamically changing clutching system.

FIG. 6 shows an exemplary relative position control process where the drive mechanism 104 mimics that of the user interface. For example, when the button 240 of the mouse 126 is depressed, the gripper 134 is in a gripped state. At index (A) the button 240 of the mouse 126 may be released and the gripper may also be in a released state. At index (B) the surgeon may move the mouse 126 forward and the gripper 134 may also be moved forward while in the released state. At index (C) the button 240 may be depressed and the gripper 134 may grip the wire 108. At index (D) the surgeon may move the mouse 126 backwards while depressing the button 240 and the gripper 134 may in turn move the wire 108 backwards. At index (E) the surgeon may release the button 240 and the gripper 134 may also be released. At indexes (F) and (G), similar to index (B) and (C), the mouse 126 may be moved forward and the gripper 134 may be in a released state until the button 240 is depressed. Thus, FIG. 6 shows a drive mechanism 104 configured to mimic the input device clutching. In this example, the first limit 302 and second limit 304 may correspond to both the user input constraints and the catheter assembly 102 constraints. That is, the line 210 may correspond to the length of the catheter assembly 102. With this approach, the user is not aware of the discontinuous nature of the drive system. The drive system in fact appears as a continuous drive system to the user because the drive system does not need to clutch within the range of motion of the input device.

FIGS. 7A and 7B show a dynamically changing clutching system. That is, the clutching location and timing thereof may be determined based on the user input at the user interface, such as the joystick 122.

FIG. 7A shows an exemplary control process for a dynamically changing clutch system when the joystick 122 is in a partial forward position 224. At index (A) the joystick 122 may be in a normal position and the gripper 134 may be gripped in a central location. At index (B) the control member 202 of the joystick 122 may move into a partial forward position 224 instructing the gripper 134 to drive the wire 108 forward. At index (C) the gripper 134 may reach the second limit 304 and release the wire 108. At index (D) the joystick 122 may still be in a partial forward position 224 and the gripper 134 may move backward to the central location. At index (E) the gripper 134 may re-grip the wire 180 and at index (F) the gripper 134 may continue to push the wire 108 forward.

FIG. 7B shows an exemplary control process for a dynamically changing clutch system when the joystick 122 is in a full forward position 222. At index (A) the joystick 122 may be in a normal position 220 and the gripper 134 may be gripped in a central position. At index (B) the control member 202 of the joystick 122 may move into a full forward position 222 instructing the gripper 134 to drive the wire 108 forward. At index (C) the gripper 134 may reach the second limit 304 and release the wire 108. At index (D) the joystick 122 may still be in a full forward position 222 and the gripper 134 may move backward to the first limit 302. At index (E) the gripper 134 may re-grip the wire 180 and at index (F) the gripper 134 may continue to push the wire 108 forward.

Thus, based on the position of the control member 202 of the joystick 122, the gripper 134 may be configured to clutch differently. For example, when a wire 108 is moving slowly forward based on the partial forward position 224 of the control member 202 the gripper 134 may clutch at the central location. This may be to allow the wire 108 to retract at a given moment without a need for the gripper 134 to re-clutch. That is, because the wire 108 is moving slowly, it may be likely that the surgeon may wish to change the direction of motion of the wire 108, e.g., from insertion to retraction, or vice versa. Accordingly, the gripper 134 may clutch at the central location as shown at index (D) to allow for this flexibility. On the other hand, if a wire 108 is moving at a faster velocity, as controlled by a full forward position 222 of the control member 202, it may be less likely that the surgeon will wish to suddenly change the direction of the wire 108, and more likely that the surgeon will continue to command movement in the same direction. Thus, the gripper 134 may clutch at the first limit 302, allowing the gripper 134 to move the wire 108 along the entire range of motion of the gripper 134 before needing to re-clutch. Thus, based on the user interaction of the user interface, the drive mechanism 104 may dynamically determine where to clutch the wire 108.

While the above examples are described with respect to the position of the control member 202, other mechanisms may be used to determine the desired velocity of the wire 108. The velocity of the wire 108 may correspond to the velocity at which the user interface is moved. For example, the speed at which the control member 202 is moved may correlate to the desired speed of the wire 108. Further, the difference between a first position of the mouse and a second position of the mouse may be used to calculate the velocity of the movement.

Figure 8:
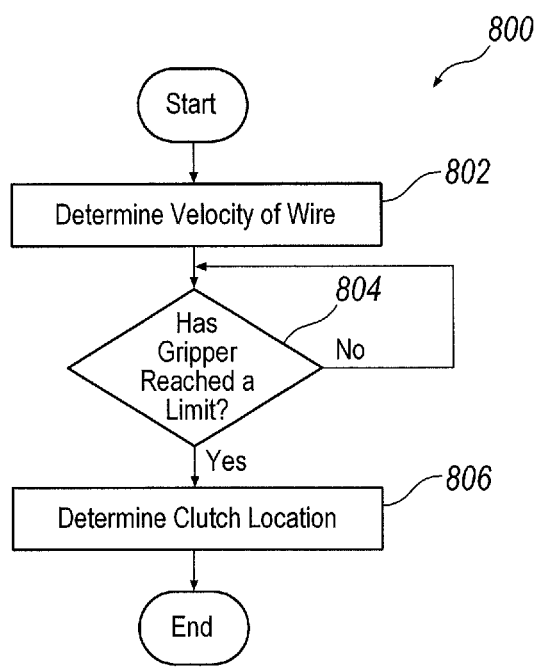
FIG. 8 illustrates an exemplary flow chart for the dynamically changing clutching system.

FIG. 8 is an exemplary flow chart showing the dynamic clutching process 800, as described above with respect to FIGS. 7A and 7B. The process begins at step 802. At step 802 a desired velocity of the wire 108 may be determined by the controller 130. As explained above, this may be determined based on a digital position of the user interface (e.g., position of the control member 202) and/or based on a difference of two positions of the user interface.

At block 804, the controller 130 may determine whether or not the gripper 134 has reached one of the first or second limits 302, 304 (e.g., as shown in index (B) of FIGS. 7A and 7B.) Additionally or alternatively, in determining whether or not the gripper 134 has reached on of the first or second limits 302, 304, the controller 130 may determine whether the gripper 134 has come within a predetermined distance of the limits 302, 304. That is, if the gripper 134 is close to one of the limits 302, 304, it may be practical for the gripper 134 to clutch and not necessarily wait until the exact limit is reached. For example, a predefined range may be established within the controller 130. If the gripper 134 comes within that predefined range, the gripper 134 may release the wire, move to accommodate further motion of the wire, and re-clutch the wire. Additionally, this predefined range may be based on the determined velocity of the wire or the position of the user interface. For example, if the gripper 134 enters the range and is travelling at a high velocity, the gripper 134 may be instructed by the controller 130 to clutch prior to it reaching the limit 302, 304. If the gripper 134 has reached one of the limits 302, 304, the gripper 134 may need to clutch in order to continue to move the wire 108 in the desired direction. Once the gripper 134 has reached one of the limits 302, 304, the process proceeds to block 806.

At block 806, the controller 130 may determine a clutch location. That is, the controller 130 may instruct the gripper 134 to un-grip the wire 108 and move to a predefined location along catheter assembly 102. Determining the predefined location may be based on the velocity at which the catheter is moving. For example, if the control member 202 of the joystick 122 is in the full forward position 222, the wire 108 may be moving at a relatively high velocity when it reaches one of the limits 302, 304 and the gripper 134 may move and clutch the wire 108 at the opposite limit. Alternatively, if the joystick 122 is in the partial forward position 224, the gripper 134 may clutch the wire 108 at the central location.

Additionally or alternatively, other factors may be used to determine when and in what position to clutch the wire. In one example, user defined preferences may be used. That is, the controller 130 may receive from the surgeon a preference to be applied when adjusting the wire. The surgeon, in one example, may prefer to have an aggressive clutching system. In another procedure the surgeon may whish to have a less aggressive clutching system in that clutching may make reversal easier (e.g., clutch to the central location instead of one of the limits).

In another exemplary configuration, the controller 130 may save a surgeons' motions in the database 132. These previously made motions may be used to predict what type of clutching to perform in future procedures. In one example, the controller may save the distance at which a wire traveled before being reversed. Thus, in future procedures, once a distance similar to the saved distance is reached, the system may prepare to clutch based on the previous motions of the surgeon.

The disclosed clutching mechanisms may also be applied to rotational ranges of motion. For example, the grippers 134 may be configured to apply a rotational motion to the wire 108. This motion may be facilitated by moving the parallel grippers 134 in opposite directions from each other. These grippers 134 may only laterally move to an extent before having to be re-adjusted in order to continue to 'roll' the wire 108. Because the user interfaces may also control the rotational movement of the wire 108, the controller 130 may also be configured to efficiently re-adjust the grippers so as to minimally affect the procedure. That is, while the wire 108 is being rotate at a high rotational velocity, the grippers may re-adjust to their full potential. On the other hand, if the rotational velocity is low, and there is a potential for the wire 108 to reverse rotational direction, the gripper 134 may be readjusted to a central location.

The process may then end.

Figure 9:
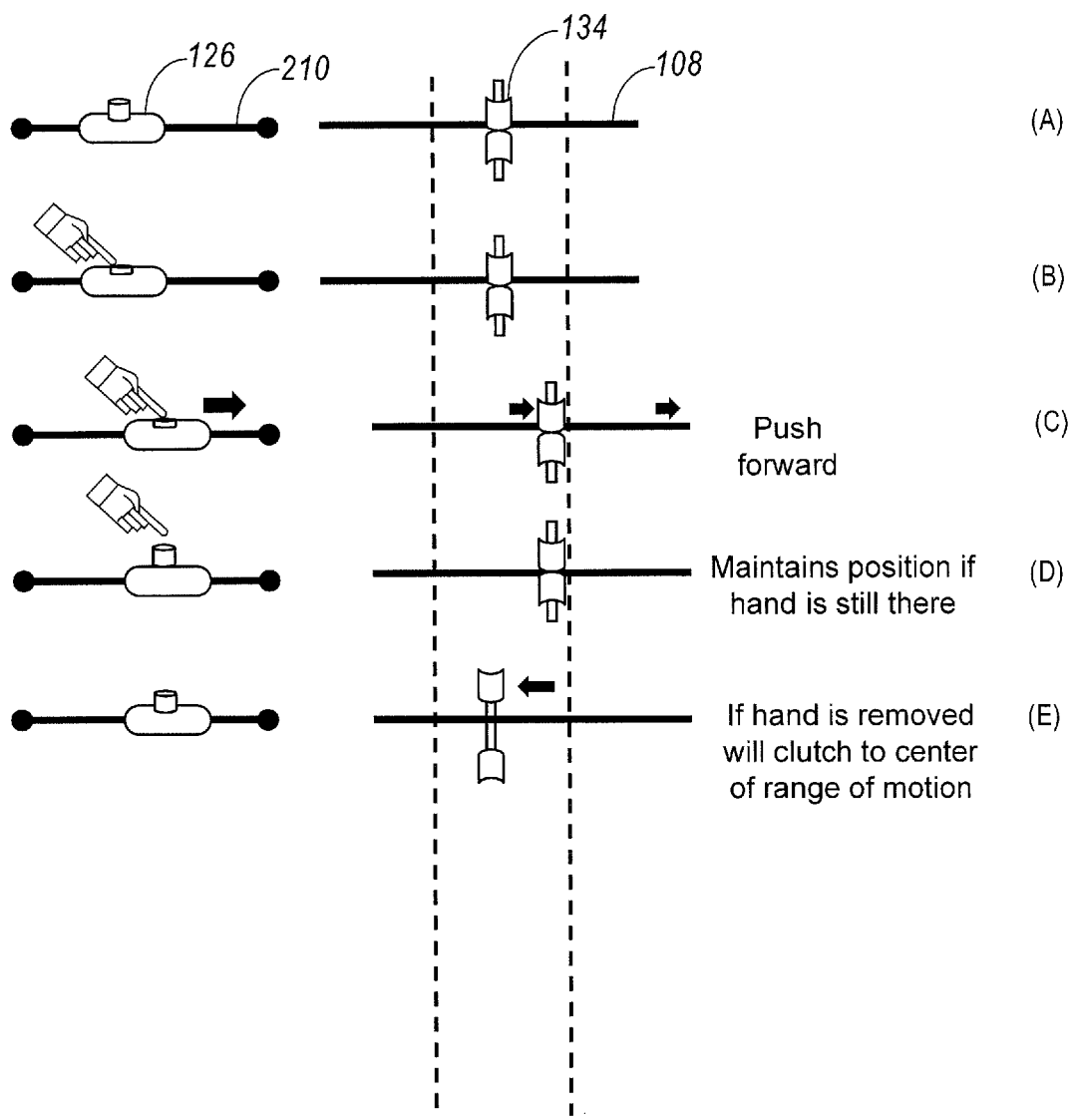
FIG. 9 illustrates an exemplary hand proximity detection process.
Figure 10:
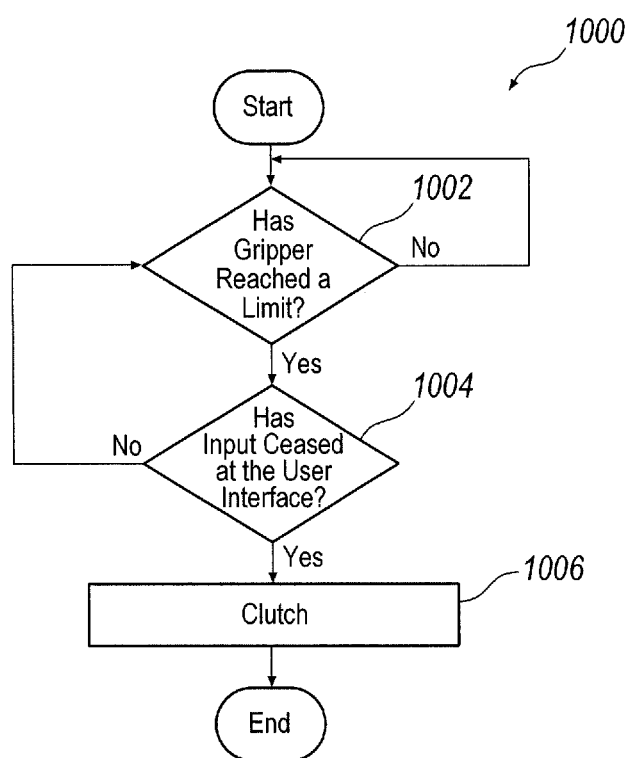
FIG. 10 illustrates an exemplary flow chart for the hand proximity detection process.

FIGS. 9 and 10 show exemplary hand proximity detection process 1000. In this process 1000, the controller 130 may instruct the drive mechanism 104 to clutch based on proximity of a surgeon's hand to the user interface. The controller 130 may use the proximity of the surgeon's hand to determine whether the user interface is in an active state or inactive state. At index (A) a gripper may be in the grip state and the user interface may be in an inactive state. At index (B) a surgeon's hand may approach the user interface and at index (C) the surgeon may push the user interface thus driving the wire 108 forward via the gripper 134. At index (D), the gripper 134 may remain in the gripped state and the user interface may remain in an active state until the surgeon's hand is removed from the user interface. At index (E), because the surgeon's hand has been removed, the user interface is inactive and the gripper 134 is configured to clutch at a predefined location.

The user interface may determine if a hand is in close proximity to it by several mechanisms. In one example, the user interface may include a biometric sensor. This sensor may include a heat sensor configured to detect the air temperature surrounding the user interface. Upon an increase in temperature, the controller 130 may determine that a surgeon's hand is in close proximity to the user interface. The biometric sensor may also include technologies such as resistive touchscreen panels, surface acoustic wave touchscreens, capacitive sensors, infrared LED and photodetectors, etc.

Additionally or alternatively, the proximity of the surgeon's hand may also be determined based on the last known contact with the user interface. After a predefined amount of time with no input from the user at the user interface (e.g. no movement of the interface or depression of the buttons 240), the controller 130 may determine that the surgeon has stepped away or at least that the surgeon has temporarily paused the procedure, thus opening a window of opportunity for the gripper 134 to clutch.

FIG. 10 shows an exemplary process 1000 beginning at block 1002. At block 1002 the controller 130 determines whether the gripper 134 has reached one of the limits 302, 304. If so the process proceeds to block 1004.

In block 1004 the controller 130 may determine whether input has ceased at the user interface. This may be determined based on the reading from the biometric sensor. Additionally or alternatively the status may be determined by the amount of input from the surgeon at the user interface. If input has ceased at the user interface, the process may proceed to block 1006. If not, it may return to block 1002.

At block 1006 the controller 130 may instruct the gripper 134 to clutch based on the absence of user interaction with the user interface.

The process may then end.

Figure 11:
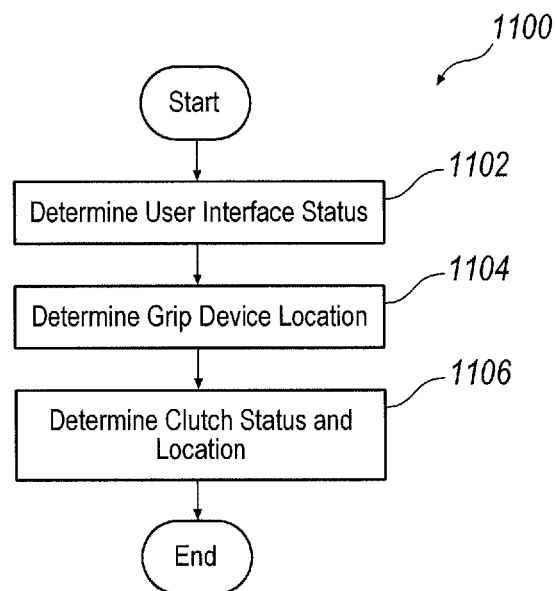
FIG. 11 illustrates an exemplary flow chart of the processes of FIGS. 3-10.

FIG. 11 shows an exemplary flow chart for a system 1100 for determining when to clutch or re-grip a wire 108 based on user input at the user interface. The process 1100 begins at block 1102. At block 1102 the controller 130 determines the user interface status based on signals from the user interface. The user interface status may include a position of the user interface (e.g., the position of the control member 202 or the location of the mouse 126 along line 210). The status may also include the velocity of the user interface (e.g., the rate at which the control member 202 or the mouse 126 is moved). The user interface status may also include the proximity of the surgeons' hand to the user interface (e.g., active, inactive.) The status may be determined by any of the above described mechanisms, or any combination thereof. Once the status is determined, the process proceeds to block 1104.

At block 1104 the location of the gripper 134 is determined. That is, the location of the gripper 134 between the limits 302, 304 may be determined.

At block 1106 the controller 130 may determine, based on the user interface status and the gripper location, the projected clutch timing and location. For example, if the user interface status is 'active' (e.g., a surgeons hand is engaging the user interface), and the gripper location has not yet reached a limit 302, 304, the controller 130 may determine that there is no need to clutch at this time. Alternatively, if the gripper location has reached a limit 302, 304, the controller 130 may instruct the gripper 134 to be released and repositioned so that the wire drive may continue. At this time, if the surgeon is still attempting to drive the wire 108, the user interface may indicate to the user, via the user interface or other mechanism, that the wire 108 is clutching.

In another example, as described above, upon determining that the wire 108 must be clutched, the location of the gripper 134 may be determined by the controller 130. That is, how far back or forward the gripper 134 may move before re-gripping the wire 108 may be determined, at least in part, based on the user interface status. For example, if the control member 202 of the joystick 122 is in the full forward position 222, the gripper 134 may be re-gripped at the first limit 302. Alternatively, if the joystick 122 is in one of the partial forward or backward positions 224, 228, the gripper 134 may be re-gripped at the central location.

In addition to determining when and where to clutch a wire 108 in a catheter assembly 102, the controller 130 may also be configured to instruct the user interface to inform the user/surgeon that the wire 108 is to be re-gripped. By indicating to the surgeon when a wire 108 will clutch, the surgeon is not surprised when the motion of the wire 108 is temporarily interrupted while the gripper 134 re-grips the wire 108. In one example, a feedback mechanism may be used to inform the user that the wire 108 is clutching. Merely by way of example, a haptic or tactile feedback, visual feedback, or audible feedback may be used to indicate that the gripper 134 is in the process of re-gripping the wire 108, or about to do so. As one example of a haptic feedback, the user interface may be prevented from moving when the wire 108 is clutching. In this example, some form of resistive mechanism may be located within the user interface and configured to receive a signal from the controller 130 to cease movement until the wire 108 clutches. In the example of the joystick 122 and/or input device 115, at least one solenoid may be arranged around the control member 202 of the joystick 122 and may be activated to hold the member 202 in place during clutching. Additionally or alternatively, as explained above, the joystick 122 may have a button (not shown). In order to resume movement of the control member 202, the button may be depressed by the surgeon to trigger the clutching. Thus, the button depression and the clutching may be synchronized. The control member 202 may be held in place until the joystick 122 instructs the wire 108 to clutch. As other examples, a warning light or audible alarm may sound in place of or in addition to haptic feedback to indicate re-gripping or the onset of re-gripping by the grippers 134.

A mouse 126 may also be capable of resisting further movement if clutching is required. For example, once the mouse 126 is at the end of line 210, the gripper 134 may also be nearing the second limit 304. If the button 240 of the mouse 126 is being depressed, the surgeon may release the button 240 and reposition the mouse 126 along the line 210. That is, the surgeon may release the button 240 and move the mouse 126 back in order to allow for more room on the table to move the mouse 126 forward again, thus allowing the wire 108 to be further driven.

Similarly, the input device 115 may also be capable of resisting further movement if clutching is required. In this example, the range of motion of the input device 115 may mimic that of the catheter assembly 102. Once the device 115 has reached its range of motion, the gripper 134 may also be nearing a limit 302, 304. Similar to the mouse, if a button of the input device is depressed, the surgeon may release the button and reposition the input device 115. Similar processes may be used with the joystick 122. For example, when the control member 202 of the joystick 122 is pushed to the full forward position 222, the control member 202 may be brought back to the center position 220 in order to further drive the wire 180 forward further.

By providing a warning, e.g., haptic resistance at the user interface, the surgeon may actively re-adjust and re-grip the wire 108 at an appropriate location. Such mechanisms may be advantageous, especially when the limits at the user interface and the catheter assembly 102 are similarly aligned. Haptic feedback may be particularly advantageous since it may allow the surgeon to receive feedback while still focusing visually and/or audibly on other aspects of the procedure.

In another example, the surgeon may not be required to actively initiate the clutching, but may simply be alerted to the fact that clutching is to occur. These cues may include any combination of visual, tactile, and audible cues. For example, an impulse or vibration may be felt at the user interface during clutching. The surgeon may also experience resistance at the user interface (e.g., control member 202 will become stiff and un-movable, etc.) The resistance may be removed when the clutching is complete. Additionally or alternatively, a second cue may indicate that clutching is complete. For example, a first vibration may indicate clutching has started and a second vibration indicates that clutching has been completed.

The surgeon may also be alerted when the wire 108 is approaching a limit 302, 304. In one example, the stiffness of the control member 202 may increase as the gripper approaches a limit 302, 304. The controller 130 may also be configured to take the velocity of the drive into consideration when applying any form of resistance to the user interface. That is, the faster the gripper 134 approaches the limit 302, 304, the faster the resistance at the user interface increases.

Visual cues may also be used, such as pulsating lights, pictures or animations of the wire 108 as it clutches. These displays may be part of the workstation 114. For example, cues may be displayed on the displays 136. These visual forms may allow the surgeon to understand the limits 302, 304 of the gripper 134 and adjust his or her procedures in view of the same.

Figure 12:
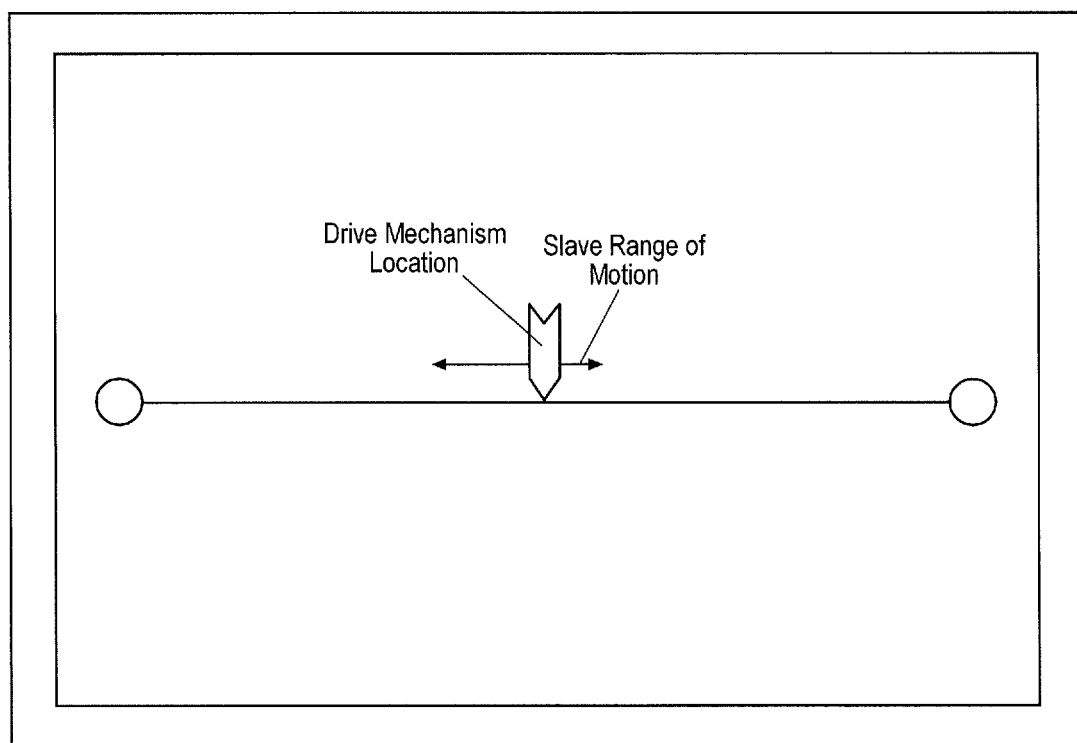
FIG. 12 illustrates an exemplary display for showing the drive mechanism and its range of motion.

An exemplary interface is shown in FIG. 12. In FIG. 12, the relationship of the ranges of motion of the user interface (e.g., the master device) and the wire 108 (e.g., the slave device) may be depicted. The current location of the drive mechanism 104 (i.e. gripper 134) may also be depicted to indicate the remaining range of motion on either end of the slave device (e.g., between the first and second limits 302, 304.) By allowing the surgeon to visualize the limits 302, 304 and the current gripping location, the surgeon may understand when to expect clutching to occur and plan accordingly.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

In general, computing systems and/or devices such as such as the controllers, biometric devices, displays telematics functions, etc., may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., the BlackBerry OS distributed by Research In Motion of Waterloo, Canada, and the Android operating system developed by the Open Handset Alliance.

Computing devices, such as the controllers, biometric devices, displays telematics functions, etc., may generally include computer-executable instructions that may be executable by one or more processors. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor or microprocessor receives instructions, e.g., from a memory or a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computing device). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions on one or more computing devices, stored on computer readable media associated therewith. A computer program product may comprise such instructions stored on computer readable media for carrying out the functions described herein. In some examples, the application software products may be provided as software that when executed by processors of the devices and servers provides the operations described herein. Alternatively, the application software product may be provided as hardware or firmware, or combinations of software, hardware and/or firmware.

What is claimed as new and desired to be protected by Letters Patent of the United States is:

1. A system, comprising:
   a drive mechanism comprising a gripper device configured to drive a medical instrument;
   a controller configured to:
      determine a user interface status;
      determine a drive mechanism location of the gripper device relative to a first limit and a second limit;
      select a clutching location of the gripper device based on the user interface status and the drive mechanism location; and
      transmit an alert to a user interface device based on the user interface status and the selected clutch location, wherein the user interface device is configured to provide an indication of the alert to a user, and wherein the alert comprises instructions that cause the user interface device to provide haptic feedback that is resistive.

2. The system of claim 1, wherein the alert comprises an indication of when the medical instrument is re-gripped by the gripper device.

3. The system of claim 1, wherein the alert comprises an indication of the onset of the gripper device re-gripping the medical instrument.

4. The system of claim 1, wherein the alert comprises an indication that the gripper device is actively clutching the medical instrument.

5. The system of claim 1, wherein the controller is configured to transmit the alert to a user interface device, and wherein the user interface device is further configured to provide an indication of the alert to a user.

6. The system of claim 5, wherein the haptic feedback facilitates preventing selection of the clutching location until the gripper device has clutched the medical instrument.

7. The system of claim 5, wherein the haptic feedback facilitates preventing selection of a clutching location while the gripper device is actively clutching the medical instrument.

8. The system of claim 5, wherein the haptic feedback facilitates preventing movement of the user interface device while the gripper device is actively clutching the medical instrument.

9. The system of claim 1, wherein the alert comprises a first alert indicative of clutching by the gripper device having started, and wherein the controller is further configured to transmit a second alert in response to the clutching by the gripper device being completed.

10. The system of claim 1, wherein the alert comprises an indication that the gripper device is nearing at least one of the first or second limit.

11. The system of claim 10, wherein the indication comprises a notification that the selection of the clutching location is required.

12. The system of claim 10, wherein the haptic feedback is configured to increase in intensity as the gripper device approaches the at least one of the first or second limit.

13. The system of claim 10, wherein the haptic feedback is configured to increase in intensity as the velocity of the gripper device increases.

14. The system of claim 1, wherein the alert comprises instructions that cause a user interface device to provide at least one of haptic feedback, visual feedback, and audible feedback based on at least one of the clutching location, the user interface status, and the drive mechanism location.

15. The system of claim 1, wherein the alert comprises instructions that cause a display of at least one of lights, pictures, and animation on at least one of a display device and a user interface device.

16. A method, comprising:
determining a user interface status;
determining a drive mechanism location of a gripper device relative to a first limit and a second limit, wherein the gripper device is configured to drive a medical instrument;
selecting a clutching location of the gripper device based on the user interface status and the drive mechanism location;
transmitting an alert to a user interface device based on the user interface status and the drive mechanism location; and
providing an indication of the alert via the user interface device, wherein the indication includes haptic feedback that is resistive.

17. The method of claim 16, wherein transmitting the alert comprises transmitting an indication of when the medical instrument is re-gripped by the gripper device.

18. The method of claim 16, wherein transmitting the alert comprises transmitting an indication of the onset of the gripper device re-gripping the medical device.

19. The method of claim 16, wherein transmitting the alert comprises transmitting an indication that the gripper device is actively clutching the medical device.

* * * * *